United States Patent [19]
Hirsch et al.

[11] Patent Number: 5,267,969
[45] Date of Patent: Dec. 7, 1993

[54] EXTERNAL RETAINING DEVICE FOR FEEDING TUBE OR THE LIKE

[75] Inventors: William H. Hirsch, Columbus; Donald J. Goldhardt, Grove City, both of Ohio

[73] Assignee: Abbott Laboratories, Abbott Park, Ill.

[21] Appl. No.: 958,374

[22] Filed: Oct. 8, 1992

[51] Int. Cl.[5] .............................................. A61M 5/32
[52] U.S. Cl. .............................. 604/174; 128/DIG. 26
[58] Field of Search ............... 604/174, 176, 180, 179; 128/DIG. 26

[56] References Cited

U.S. PATENT DOCUMENTS

| | | | |
|---|---|---|---|
| 4,261,363 | 4/1981 | Russo | 604/174 |
| 4,419,094 | 12/1983 | Patel | 604/165 |
| 4,435,174 | 3/1984 | Redmond et al. | 604/174 |
| 4,533,349 | 8/1985 | Bark | 604/180 |
| 4,645,492 | 2/1987 | Weeks | 604/174 |
| 4,666,433 | 5/1987 | Parks | 128/DIG. 26 |
| 4,717,385 | 1/1988 | Cameron et al. | 604/174 |
| 4,886,508 | 12/1989 | Washington | 604/327 |
| 5,073,166 | 12/1991 | Parks et al. | 604/93 |
| 5,084,024 | 1/1992 | Skinner | 604/175 |

OTHER PUBLICATIONS

Sales Literature for "The Nuport ® Peg" from Sandoz Nutrition, undated, which shows an external retaining device & feeding tube.
Sales literature for feeding tubes from Sandoz Nutrition, 1991, which shows an external retaining device & feeding tube.

Primary Examiner—John G. Weiss
Attorney, Agent, or Firm—Lonnie R. Drayer; Donald O. Nickey

[57] ABSTRACT

An external retaining device may be used for securing an enteral feeding tube in a desired location with respect to a person's skin. The feeding tube passes through a first hole in the retaining device, then is guided through a 90°, bend following a radius of curvature such that the feeding tube is not kinked, and then passes through a second hole in the retaining device, with the longitudinal axes of the holes in the retaining device being coplanar and oriented perpendicular to one another.

17 Claims, 6 Drawing Sheets

EXTERNAL RETAINING DEVICE FOR FEEDING TUBE OR THE LIKE

FIELD OF INVENTION

The present invention relates to a device for securing a feeding tube, such as a gastrostomy tube or a jejunostomy tube, in place with respect to an opening in a person's skin. The present invention also relates to the assembly of an external retaining device and a feeding tube.

BACKGROUND OF THE INVENTION

Most patients in health care facilities are able to achieve sufficient caloric intake through eating prepared meals. However, a sizeable number of patients are unable to orally ingest foods due to conditions such as facial injuries, esophageal injuries, or unconsciousness. In response to this problem, liquid foods have been developed for enteral feeding. Enteral feeding often utilizes a feeding tube which passes through a patient's skin into either the stomach or intestine. It is important to secure such a feeding tube in place and this may be accomplished through a combination of retaining members located internally and externally of the patient. There is provided in accordance with the present invention an external retaining device which solves several problems which are present in prior art retaining devices which will be described herein with respect to the drawings which form a part of this specification.

BRIEF DESCRIPTION OF THE DRAWINGS

The features of the invention which are believed to be novel are set forth with particularity in the appended claims. The present invention, both as to its structure and manner of operation, may best be understood by referring to the following detailed description, taken in accordance with the accompanying drawings in which:

DETAILED DESCRIPTION OF THE INVENTION

Figure 1:
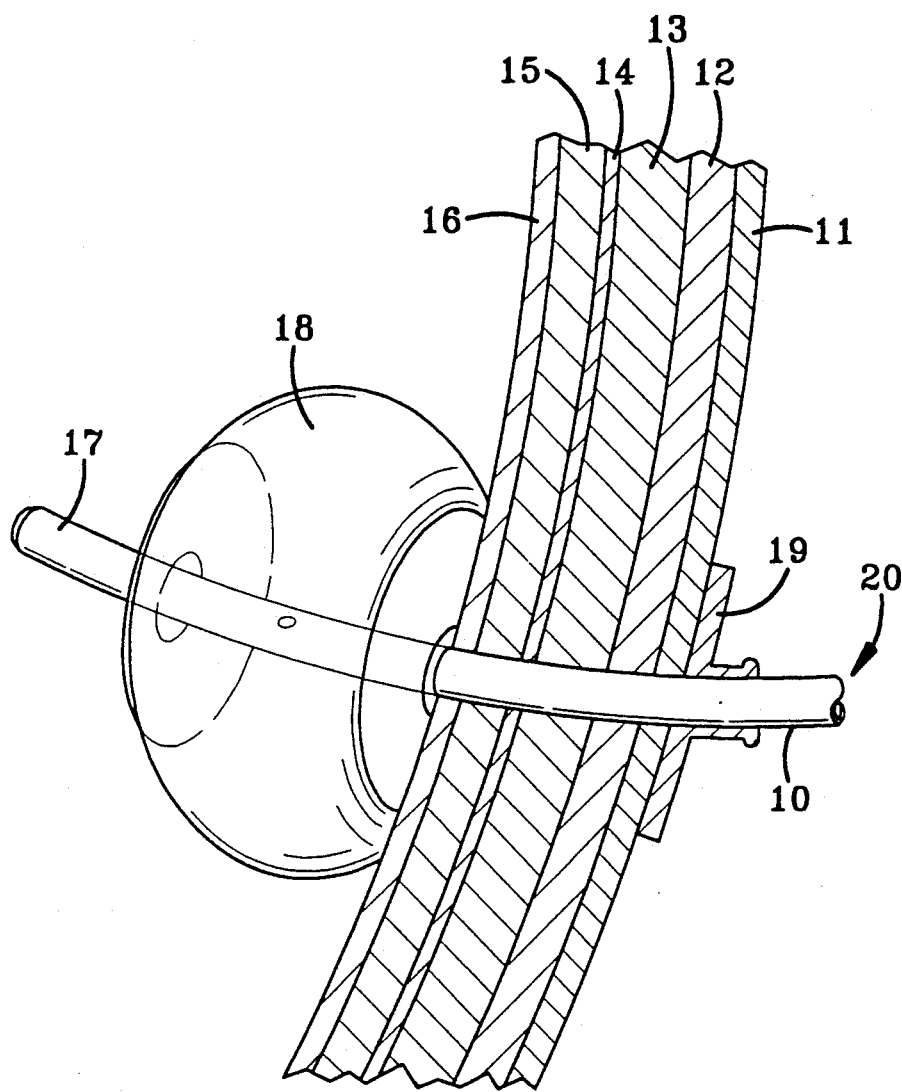
FIG. 1 is a pictorial representation of a gastrostomy tube using a prior art external retaining device.

Referring first to FIG. 1 there is shown a gastrostomy tube 10 which has been placed in a person for introducing a liquid nutritional product into the stomach of a person. The gastrostomy tube 10 extends through the epidermis 11, the fat layer 12, the muscle layer 13, the peritoneum 14, the stomach lining 15, and the gastric mucosa 16. One end 17 of the gastrostomy tube is located within the person's stomach. An expandable member 18 is located within the stomach, adjacent to the mucosa wall 16, and functions as an internal retaining member to reduce the chances of an unplanned removal of the gastrostomy tube from the person's stomach. An external retaining device 19 is located externally of the person adjacent to the epidermis 11. This particular external retaining device is a prior art disk shaped member which functions to maintain the gastrostomy tube substantially perpendicular to the person's skin. Such a prior art external retaining device is employed for example in gastrostomy tubes which have been distributed by Sandoz Nutrition Corporation, 5320 West Twenty Third Street, P.O. Box 370, Minneapolis, Minn. 55440, U.S.A., under trade names such as CALUSO ® PEG and SUPER PEG ™. While the Sandoz enteral retaining device has a base portion that is round, other shapes such as a triangular device taught in the U.S. Pat. 5,071,405 are of similar structure. The disadvantages of such a prior art external retaining devices for a feeding tube is that the portion 20 of the feeding tube which is external of the person's body include: (a) unless the feeding tube is taped to the person's skin the tube can easily become tangled in the person's clothing or pulled by an incoherent person; (b) if the tube is taped to the persons's skin it must be shaped into a loop, which could kink the tube closed or at least reduce the effective cross-sectional area of the tube and restrict the flow of liquid through the tube; and (c) if a person should pull on the tube it will exert a force on the internal retaining device 18 perpendicular to the person's tissues and could result in an unintentional removal of the feeding tube from the stomach.

Figure 2:
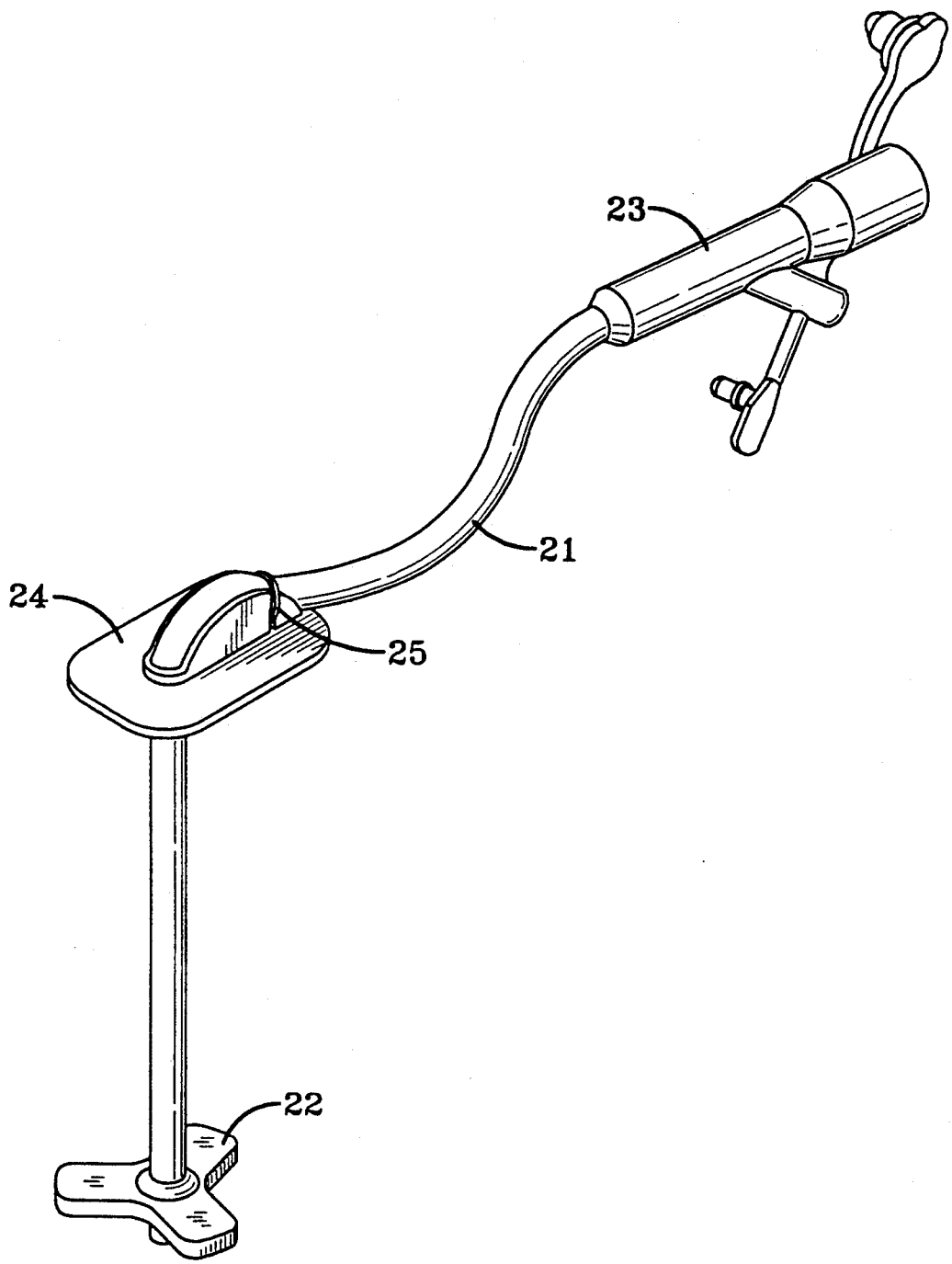
FIG. 2 is a pictorial representation of a gastrostomy tube using another prior art external retaining device.

Referring next to FIG. 2 there is shown a gastrostomy tube 21 having an internal retaining member 22 located near one end and a Y-port 23 near the other end for connecting the gastrostomy tube to a source of a liquid nutritional product. This particular feeding tube employs an external retaining device 24 which can be placed adjacent to a person's skin and directs the protruding tube back towards the person's skin. A ratcheted tie 25 secures the feeding tube 21 in an arcuate channel formed in the external retaining device. Such a prior art external retaining member has been marketed by Sandoz Nutrition as a component of a feeding tube product marketed under the trade name NUPORTO ® PEG. The problems encountered with this prior art external retaining device include: (a) any significant change in the person's weight could require an adjustment in the location along the tube of the external retaining device and in order to move the external retaining member the ratcheted tie must be severed and replaced, which requires maintaining a supply of the ratcheted ties; and (b) a patient that is not rational could pull on the ratcheted tie and interrupt the flow of nutritional product through the feeding tube, necessitating replacement of the ratcheted tie.

Figure 3:
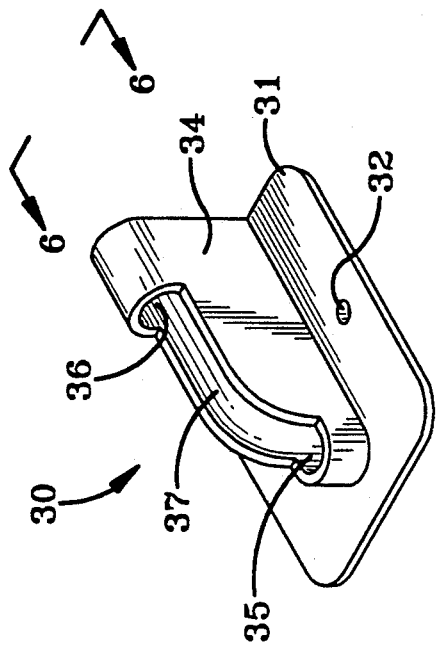
FIGS. 3-6 are a variety of views of a preferred embodiment of an external retaining device in accordance with a preferred embodiment of the present invention.
Figure 6:
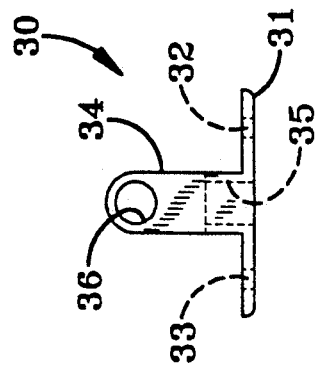
Figure 5:
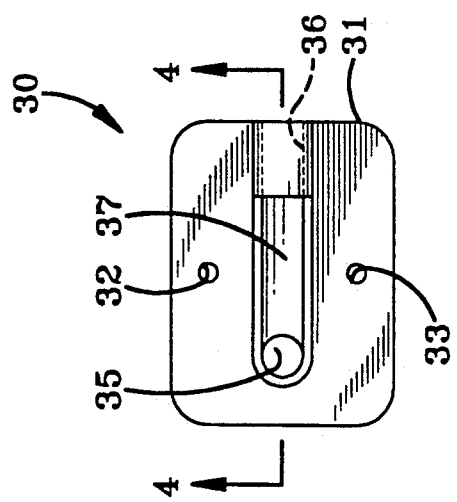
Figure 4:
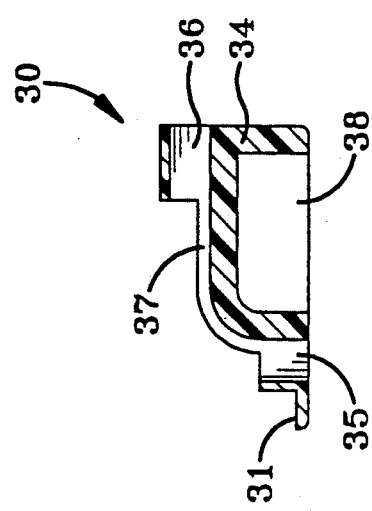

Referring next to FIGS. 3-6 there are presented several views of an external retaining device 30 for a feeding tube in accordance with the preferred embodiment of the present invention, to wit: FIG. 3 is a perspective view; FIG. 5 is a top view; FIG. 4 is a cross sectional view looking in the direction of the arrows of line 4—4 in FIG. 5; and FIG. 6 is an end view looking in the direction indicated by the arrows 6 in FIG. 3.

The external retaining device, sometimes referred to in the medical device trade as a skin disk, comprises a substantially flat base portion 31 having a tube guiding portion 34 extending from one side thereof. As used herein and in the claims, all terms such as "top", "bottom", "upper", "lower", "vertical" and "horizontal"

when used with respect to the retaining device of the present invention are understood to refer to a retaining device resting on a flat horizontal surface with the tube guiding portion 34 extending upwardly from said flat horizontal surface. Preferably, the external retaining device is a single molded piece, while it is recognized to be within the scope of the invention to make the base portion and tube guiding portions separately and thereafter join them together, for example with a suitable adhesive. Preferably the external retaining device is molded as a single piece from silicone rubber, polyvinyl chloride, or any other soft elastomeric material which is not an irritant to a person's skin. While the base portion 31 is shown as being rectangular with rounded corners, it is understood that the base portion may be circular, triangular, or any desired shaped. While the bottom surface of the base portion is shown as being substantially flat, as in FIG. 6, it is understood that the bottom surface could, if desired, be corrugated to allow the access of air to the underlying skin. Furthermore, while it is considered to be good manufacturing and design practice to have an indent 38 in the underside of the tube guiding portion, as best shown in FIG. 4, it is within the scope of the invention to eliminate the indent so that the device has a more solid and rigid structure.

In a preferred embodiment the base portion of the device has upper and lower surfaces which are parallel to one another, as shown in FIGS. 3, 4 and 6, but it is within the scope of the invention to have either one or both of these surfaces curved. In a preferred embodiment the base portion has at least one hole 32, 33 formed therein to facilitate suturing the external retaining device to a person's skin. However, it is understood that while providing the holes for suturing is optional, it is desirable because the holes 32, 33 which are preferably formed during a molding process tend to reduce the tearing of the base portion when stresses are placed on the sutures.

Figure 7:
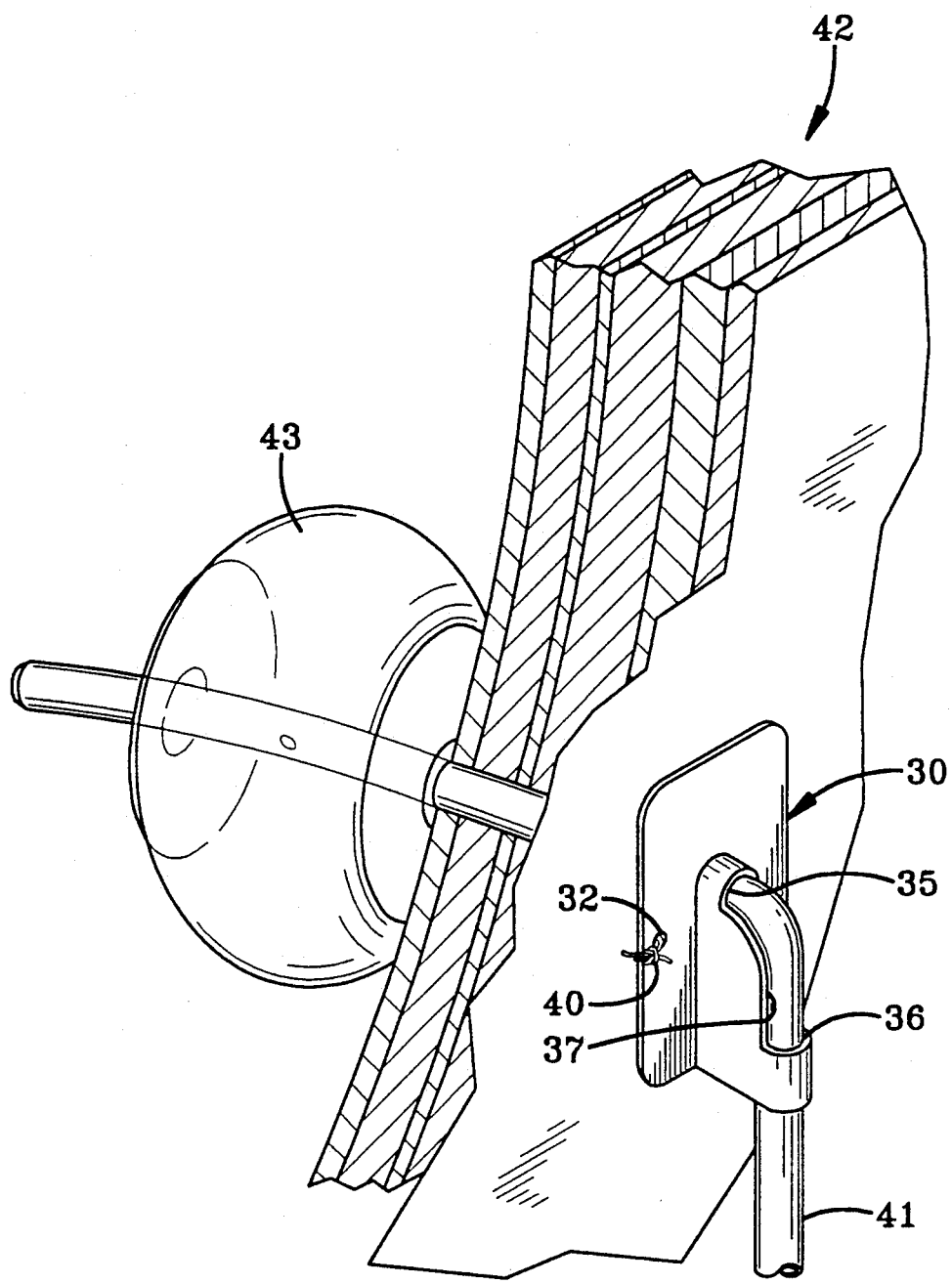
FIG. 7 is a pictorial representation of a gastrostomy tube employing an external retaining device in accordance with the present invention.

The external retaining device has a vertical hole 35 and a horizontal hole 36 formed therein, with a tube guiding channel 37 extending therebetween. The tube guiding channel has an external surface which is concave so as to be complementary to the external surface of a tube which is received in the channel. The use of the external retaining device of the present invention may be better understood by referring to FIG. 7 in conjunction with FIGS. 3-6. A gastrostomy tube 41 extends from outside of a person through several layers 42 of body tissue (which were described in greater detail above with respect to FIG. 1) into a person's stomach. An internal retaining member 43, which in this embodiment is a balloon which is well known in the art, is disposed adjacent to the mucosa of the stomach. The bottom side of the external retaining device is against the person's skin and is preferably secured thereto by one or more sutures 40 which extend through the holes 32, 33 formed in the base portion 31 of the external retaining device. The hole 35 (which is oriented vertically in FIGS. 3-6) is aligned with the stoma through which the gastrostomy tube extends. The gastrostomy tube passes through the base portion of the external retaining device via the hole 35, then is disposed within the tube guiding channel 37, and then passes through a hole 36 (which is oriented horizontally in FIGS. 3-6). Put another way, the feeding tube passes through a first hole 35, then as guided through a 90° bend following a radius of curvature such that the tube is not kinked, and then passes through a second hole 36, with the longitudinal axes of the holes being coplanar and oriented perpendicular to one another. Put yet another way, going along the feeding tube towards the stoma through the person's tissues, a feeding tube enters the external retaining device through a first hole 36 with extends substantially parallel to the person's skin, then is disposed within a channel 37 which guides the feeding tube in an unkinked condition through a 90°, turn, then the feeding tube exits the external retaining device via a second hole 35 which is oriented substantially perpendicular to the person's skin and is aligned with the stoma. The channel 37 is of sufficient depth that it prevents the lateral movement of the portion of the feeding tube which is disposed therein.

The diameters of the holes in the external retaining device, with respect to the outside diameter of the feeding tube, is believed to be important to the proper functioning of the device. For example, an external retaining device made of silicone rubber may be used with a size 20 French (0.263' outside diameter) silicone rubber feeding tube. The inside diameter of the hole 35 which will be perpendicular to the person's skin may be about 0.230' so that there is a very slight interference fit, while the inside diameter of the hole 36 which will be perpendicular to the person's skin may be about 0.280' so that there is no interference between the feeding tube and the external retaining device when the feeding tube passes through this hole. Of course, it is understood that the relative sizes of the holes and feeding tube may be varied depending upon the materials of which they are made and the desires of the manufacturer and user.

The external retaining device of the present invention therefore functions not only as a retaining device, but also as an anti-kinking device. Furthermore, the location of the external retaining device relative to the feeding tube can be adjusted without having to replace a ratcheted tie as in the prior art device shown in FIG. 2. Furthermore, there is no loop in the feeding tube for an incoherent person to pull on, as when the feeding tube of FIG. 1 is looped and taped to a person's skin. Yet another advantage of the external retaining device of the present invention is that if the portion of the feeding tube which extends externally of the person beyond the retaining device is pulled upon, the feeding tube does not slip easily through the external retaining device and the force exerted upon an internal retaining device 43 is not fully exerted in a direction parallel to the stoma, so that the likelihood of an unintentional removal of the feeding tube from the stomach is decreased.

Figure 9:
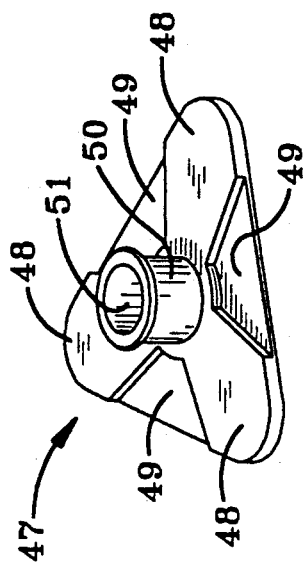
FIGS. 8 and 9 present another embodiment of a gastrostomy tube employing an external retaining device in accordance with the present invention.
Figure 8:
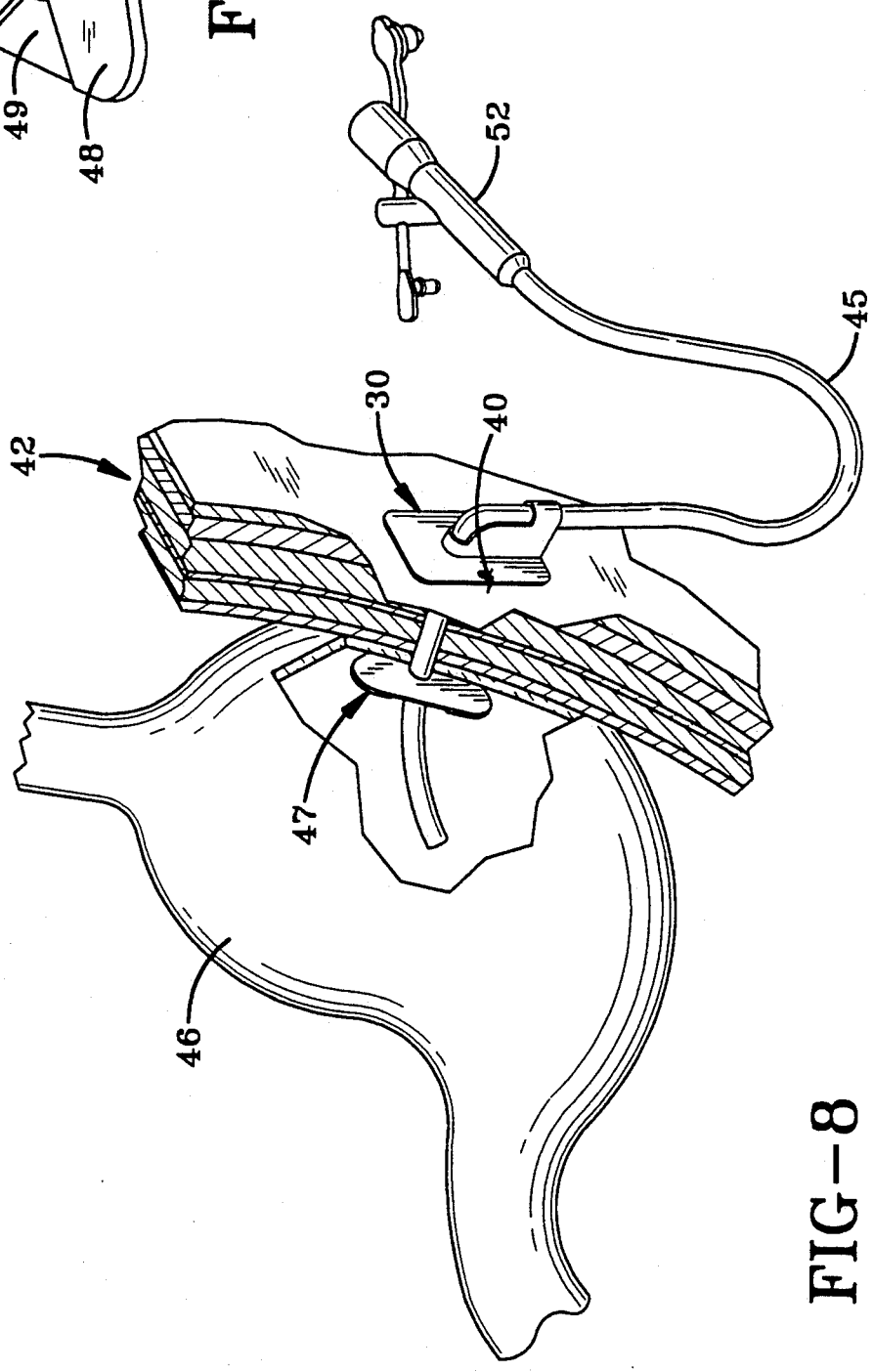

Referring next to FIGS. 8 and 9 there is shown a gastrostomy tube 45 which passes through a person's tissues 42 (which were described in greater detail above with respect to FIG. 1) via a stoma to enter the stomach 46. This gastrostomy tube has an internal retaining member 47 which is of a different structure from the internal retaining member illustrated in FIG. 7. This gastrostomy tube has an internal retaining member 47 of the type taught in commonly owned U.S. Pat. No. 5,080,650. That is to say, as best shown in FIG. 9, the internal retaining element 47 is formed of an elastomeric material and comprises three resilient petaloid flanges 48 extended from a tubular hub 50, which has a bore 51 extending therethrough, with substantially triangular connecting portions 49 interposed between and connecting each pair of next adjacent petaloid flanges 48. The connecting portions 49 may be thinner than the petaloid flanges 48, as shown in FIG. 9, and may be formed of a different material from the petaloid flanges.

However, in any case it is clear that an external retaining device 30, according to the present invention, shown secured in place by sutures 40, may be used in conjunction with an internal retaining member which is either expandable or non-expandable. It is also to be noted in FIG. 8 that a feeding tube 45 assembly in accordance with the invention preferably includes means for connecting the feeding tube to a source of liquid nutrition, for example a Y-port 52. Such a Y-port is taught in commonly owned U.S. Design Pat. No. 308,576, as well as in commonly owned U.S. Pat. No. 5,057,093.

Figure 10:
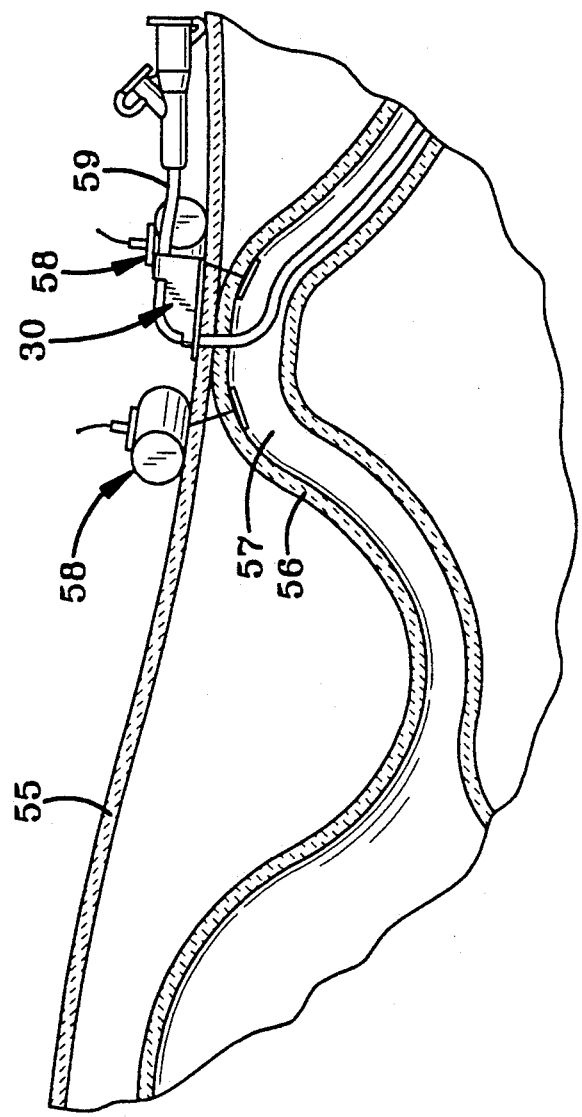
FIG. 10 is a pictorial representation of a jejunostomy tube employing an external retaining device with the present invention.

Yet another application of the external retaining member of the present invention is presented in FIG. 10 which shows the use of the new external retaining member 30 in conjunction with a jejunostomy tube 59. The jejunostomy tube 59 passes through the abdominal wall 55, intestinal wall 56 and is located in the jejunum 57. The intestine is secured adjacent to the abdominal wall using T-Fastener assemblies 58, of the type taught in U.S. Pat. RE 34,021. A jejunostomy tube has a much smaller diameter than a gastrostomy tube, and the dimensions of the external retaining device 30 of the present invention must be adjusted accordingly. It is to be noted from FIG. 10 that no internal retaining device is used in conjunction with the jejunostomy tube.

The peristaltic action of the intestines may exert forces on the jejunostomy tube which tend to cause a portion of the tube to back-out of the body via the stoma. The interference fit between the tube and the external retaining device at the vertical hole in the external retaining device tends to minimize the amount of tube back-out, and tends to prevent the backed-out portion of the tube from kinking.

It is thus apparent that an external retaining device, according to the present invention, solves several problems that were present in the prior art devices and that an assembly of the new external retaining device and a tube for enteral feeding has utility for feeding a person.

While certain representative embodiments and details have been described for the purpose of illustrating the invention, it will be apparent to those skilled in the art that various changes and modifications may be made therein without departing from the spirit or scope of the invention.

We claim:

1. An external retaining device for use with a feeding tube comprising a base portion and a tube guiding portion extending upwardly from the base portion, said base portion and tube guiding portion having a vertically extending hole therethrough, said tube guide portion having a horizontally extending hole therethrough, said vertical and horizontal holes having longitudinal axes which are coplanar and oriented perpendicular to one another, said vertical and horizontal holes communicating with one another by means of a concave tube guiding channel in said tube guiding portion which extends between said holes, said tube guiding channel being oriented such that a continuous tubular member may pass through both of said holes and rest in said tube guiding channel with the longitudinal axis of the tubular member lying in the same plane as the longitudinal axes of said holes.

2. An external retaining device for use with a feeding tube according to claim 1 wherein said base portion has at least one additional hole formed therein to facilitate suturing the external retaining device to a person.

3. An external, retaining device for use with a feeding tube according to claim 1 wherein the internal diameter of said vertically extending hole is smaller than the internal diameter of said horizontally extending hole.

4. An external retaining device for use with a feeding tube according to claim 2 wherein the internal diameter of said vertically extending hole is smaller than the internal diameter of said horizontally extending hole.

5. An external retaining device for use with a feeding tube according to claim 1 wherein said tube guiding channel has an external surface which is concave so as to be complementary to an external surface of a tube which is received in the channel.

6. An external retaining device for use with a feeding tube according to claim 2 wherein said tube guiding channel has an external surface which is concave so at to be complementary to an external surface of a tube received in the channel.

7. An external retaining device for use with a feeding tube according to claim 3 wherein said tube guiding channel has an external surface which is concave so at to be complementary to an external surface of a tube received in the channel.

8. An external retaining device for use with a feeding tube according to claim 4 wherein said tube guiding channel has an external surface which is concave so at to be complementary to an external surface of a tube received in the channel.

9. An assembly of an enteral feeding tube and an external retaining device, said enteral feeding tube comprising a continuous hollow tubular member having a longitudinal axis and first and second ends, said external retaining device comprising a base portion and a tube guiding portion extending upwardly from the base portion, said base portion and tube guiding portion having a vertically extending hole therethrough, said tube guiding portion having a horizontally extending hole therethrough, said vertical and horizontal holes having longitudinal axes which are coplanar and oriented perpendicular to one another, said vertical and horizontal holes communicating with one another by means of a concave tube guiding channel in said tube guiding portion which extends between said holes, said tubular member being disposed within said tube guiding channel and extending through both said vertical and horizontal holes with the longitudinal axis of the tubular member lying in the same plane as the longitudinal axes of said holes.

10. An assembly of an enteral feeding tube and an external retaining device according to claim 9 wherein the feeding tube is a gastrostomy tube and further comprises an internal retaining device.

11. An assembly of an enteral feeding tube and an external retaining device according to claim 10 wherein the internal retaining device is expandable.

12. An assembly of an enteral feeding tube and an external retaining device according to claim 9 wherein the feeding tube is a jejunostomy tube.

13. An assembly of an enteral feeding tube and an external retaining device according to claim 9 wherein the base portion of the external retaining device has at least one additional hole formed therein to facilitate suturing the device to a person.

14. An assembly of an enteral feeding tube and an external retaining device according to claim 9 wherein the internal diameter of said vertically extending hole is smaller than the internal diameter of said horizontally extending hole.

15. An assembly of an enteral feeding tube and an external retaining device according to claim 10 wherein the internal diameter of said vertically extending hole is smaller than the internal diameter of said horizontally extending hole.

16. An assembly of an enteral feeding tube and an external retaining device according to claim 15 wherein the internal retaining device is proximal to the vertically extending hole of the external retaining device.

17. An assembly of an enteral feeding tube and an external retaining device according to claim 13 wherein the internal diameter of said vertically extending hole is smaller than the internal diameter of said horizontally extending hole.

* * * * *

UNITED STATES PATENT AND TRADEMARK OFFICE
CERTIFICATE OF CORRECTION

PATENT NO. : 5,267,969
DATED : December 7, 1993
INVENTOR(S) : W. Hirsch, D. Goldhardt It is certified that error appears in the above-identified patent and that said Letters Patent is hereby corrected as shown below:

Title page, col. 2,
In the fifth line of the Abstract delete the "," which follows "90°".

Column 2, line 43, "NUPORTO®" should be --NUPORT®--.

Column 4, line 8, "90°, turn" should be --90° turn--.

Column 4, line 20, "0.263'" should be --0.263"--.

Column 4, line 23, "0.230'" should be --0.230"--.

Column 4, line 25, "0.280'" should be --0.280"--.

Signed and Sealed this

Seventeenth Day of May, 1994

Attest:

BRUCE LEHMAN

*Attesting Officer*     *Commissioner of Patents and Trademarks*